United States Patent
Hagiwara et al.

(10) Patent No.: US 7,580,501 B2
(45) Date of Patent: Aug. 25, 2009

(54) CT IMAGE RECONSTRUCTION METHOD, CT APPARATUS, AND PROGRAM

(75) Inventors: Akira Hagiwara, Tokyo (JP); Makoto Gohno, Tokyo (JP); Mitsuru Yahata, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 87 days.

(21) Appl. No.: 11/214,503

(22) Filed: Aug. 30, 2005

(65) Prior Publication Data
US 2006/0050838 A1    Mar. 9, 2006

(30) Foreign Application Priority Data
Sep. 1, 2004    (JP)    ............... 2004-254536

(51) Int. Cl.
*A61B 6/03* (2006.01)
(52) U.S. Cl. ............................. 378/19; 378/4
(58) Field of Classification Search ............ 378/4, 378/15, 19, 901; 382/275, 300, 128–131
See application file for complete search history.

(56) References Cited

U.S. PATENT DOCUMENTS

| | | | | |
|---|---|---|---|---|
| 4,178,510 A | * | 12/1979 | Wagner | ............ 378/51 |
| 5,229,934 A | * | 7/1993 | Mattson et al. | ............ 600/425 |
| 5,377,250 A | * | 12/1994 | Hu | ............ 378/15 |
| 6,343,108 B1 | * | 1/2002 | Heuscher | ............ 378/4 |
| 6,449,337 B1 | * | 9/2002 | Honda et al. | ............ 378/117 |
| 6,529,575 B1 | * | 3/2003 | Hsieh | ............ 378/4 |
| 6,865,247 B2 | | 3/2005 | Hagiwara | |
| 2004/0222380 A1 | * | 11/2004 | Fuchs et al. | ............ 250/369 |

FOREIGN PATENT DOCUMENTS

| | | |
|---|---|---|
| JP | 2003-116841 | 4/2003 |
| WO | WO03/024332 A2 * | 3/2003 |

OTHER PUBLICATIONS

Kak et al., Principles of Computerized Tomographic Imaging, 1988, IEEE Press, ISBN 0-87942-198-3, pp. i-xii, ix, x, and 49-112.*
Akira Hagiwara; X-Ray CT System; U.S. Appl. No. 10/892,426, filed Jul. 15, 2004; 21 pgs.
Akira Hagiwara et al; Radiation Computed Tomopgraphy Apparatus; U.S. Appl. No. 10/828,456, filed Apr. 20, 2004; 29 pgs.
Kotoko Morikawa et al.; Radiation Computed Tomography Apparatus and Tomographic Image Producing Method; U.S. Appl. No. 10/827,932, filed Apr. 20, 2004; 38 pgs.
Akihiko Nishide et al; X-Ray Ct Imaging Method and X-Ray CT System; U.S. Appl. No. 10/885,189, filed Jul. 6, 2004; 35 pgs.

* cited by examiner

*Primary Examiner*—Edward J Glick
*Assistant Examiner*—John M Corbett
(74) *Attorney, Agent, or Firm*—Armstrong Teasdale LLP

(57) ABSTRACT

A CT image reconstruction method includes substituting other projection data, which has a predetermined positional relationship to projection data that is found defective during scanning, for the defective data, and interpolating back projection data using a value and information on a scanned position that are contained in the substitute data.

18 Claims, 4 Drawing Sheets

CT IMAGE RECONSTRUCTION METHOD, CT APPARATUS, AND PROGRAM

CROSS REFERENCE TO RELATED APPLICATIONS

This application claims the benefit of Japanese Application No. 2004-254536 filed Sep. 1, 2004.

BACKGROUND OF THE INVENTION

The present invention relates to a CT image reconstruction method, a CT apparatus, and a program. More particularly, the present invention relates to a CT image reconstruction method, a CT apparatus, and a program for interpolating back projection data, which represents each slice plane, using projection data items produced by scanning a subject, and reconstructing a CT image on the basis of the back projection data.

In X-ray CT apparatus, a subject is scanned with an X-ray fan-shaped beam, and an X-ray detector having numerous (for example, 1000) detector elements set in array detects X-rays transmitted by the subject. The subject is intermittently or continuously moved in the directions of the body axis according to an axial or helical scan technique, whereby all projection data items representing a specific scan field are acquired and stored. Back projection data required for reconstruct an image is read or interpolated for each slice plane, and a CT image of the subject is reconstructed based on the back projection data.

In recent years, along with the tendency towards an X-ray detector having more channels and more detector arrays (16 detector arrays), the frequency of occurrence of a defect such as poor sensitivity in a detector element or detector data (which refers to projection data) has increased. If defective data is used to reconstruct an image, a tomographic image is affected by a ring artifact or the like. The defective data should therefore be compensated by other detector data.

In order to compensate defective data caused by microscopic discharge of an X-ray tube, a conventionally known X-ray CT apparatus interpolates projection data, which is contained in a view that cannot be produced normally, using projection data items contained in views preceding or succeeding the view in an X-axis direction, projection data items contained in an opposite view, or projection data items produced at the same view angle as the view angle, at which the view is produced, during scans preceding or succeeding in a body-axis direction the scan during which the view is produced (Patent Document 1).

[Patent Document 1] Japanese Unexamined Patent Application Publication No. 2003-116841 (Claims 1, 3, and 4)

According to the technique of interpolating defective data itself, when back projection data representing each slice plane whose image is reconstructed is interpolated, pieces of positional information (channel numbers and view angles) on normal projection data items used to interpolate the defective data are lost. Therefore, the back projection data contains inconsistent positional information.

The above drawback will be described with reference to drawings. Referring to FIG. 4, reference numeral 40 denotes an X-ray tube, reference numeral 90 denotes an X-ray detector, and reference numeral 100 denotes a subject. Assume that projection data g (CH3,Vj) produced by a channel CH3 and contained in a view Vj is defective. Conventionally, projection data items g(CH2,Vi) and g(CH4,Vk) contained in views Vi and Vk preceding or succeeding the view Vj in which the defective data is contained are summated at a predetermined ratio in order to produce interpolated data g'(CH3,Vj).

However, the defective data g(CH3,Vj) stems from a signal having transmitted along a line Lj. The projection data items g(CH2,Vi) and g(CH4,Vk) stem from signals having transmitted along lines Li and Lk respectively. Strictly speaking, the signals are different from one another in terms of a path along which a signal is transmitted by the subject 100 (a region).

Referring to FIG. 3, back projection data h(CH3,Vj) is interpolated in order to represent each position on each slice plane Si for the purpose of image reconstruction. Conventionally, a count value alone is taken into account. Interpolated data g'(CH3,Vj) resulting from interpolation is used as projection data, which is supposed to be produced by a channel CH3 and contained in the view Vj, in order to interpolate back projection data. The attributes (especially, pieces of positional information) of the projection data items g(CH2,Vi) and G(CH4,Vk) that are used to interpolate the data g'(CH3, Vj) are not reflected on production of back projection data. This deteriorates the quality (faithfulness) of a reconstructed image.

SUMMARY OF THE INVENTION

Therefore, an object of the present invention is to provide a CT image reconstruction method, a CT apparatus, and a program capable of faithfully reflecting the attribute (value and positional information) of substitute data, which is used to compensate defective data, on production of image reconstruction data.

The above object is accomplished by a technique illustratively shown in FIG. 3. Namely, a CT image reconstruction method according to the first aspect of the present invention comprises the steps of: interpolating back projection data, which is required for reconstruction of a CT image, using projection data items produced by scanning sections of a subject preceding and succeeding a section concerned; and reconstructing a tomographic image of the subject using the interpolated back projection data. Projection data g(CH2,Vi) or g(CH4,Vk) having a predetermined positional relationship to projection data g(CH3,Vj) that is found defective during scanning is substituted for the defective projection data g(CH3,Vj). A value and information on a scanned position (channel and view) contained in the substitute data are used to interpolate back projection data h(CH, Vj). Consequently, the value and scanned position contained in the substitute data are faithfully reflected on interpolation of back projection data. An image is reconstructed more accurately.

A CT apparatus in accordance with the second aspect of the present invention interpolates back projection data, which is required for reconstruction of a CT image, using projection data items that are produced by scanning sections of a subject preceding and succeeding a section concerned, and reconstructs a tomographic image of the subject according to the interpolated back projection data. The CT apparatus comprises: a data substitution means for substituting projection data, which has a predetermined positional relationship to projection data found defective during scanning, for the defective projection data; and a data interpolation means for interpolating back projection data using a value and information on a scanned position which are contained in the substitute data. Consequently, the value and scanned position contained in the substitute data are faithfully reflected on interpolation of back projection data. Eventually, an image can be reconstructed more accurately.

According to the third aspect of the present invention, the data substitution means included in the CT apparatus in accordance with the second aspect of the present invention substitutes projection data g(CH2,Vi) or g(CH4,Vk), which is contained in a view Vi or Vk preceding or succeeding a view Vj containing projection data g(CH3,Vj) found defective during scanning and which is produced on a channel CH2 or CH4 adjoining a channel on which the defective data is produced, for the defective data g(CH3,Vj). Consequently, the projection data g(CH2,Vi) or g(CH4,Vk) stemming from signals transmitted along paths that are close to a path, along which a signal providing the defective data is transmitted, in a body-axis direction is substituted for the defective data g(CH3,Vj). Positional information on the substitute data is faithfully reflected on production of back projection data h(CH3,Vj).

According to the fourth aspect of the present invention, the data substitution means included in the CT apparatus in accordance with the second aspect of the present invention substitutes projection data g(CH2,Vj) or g(CH4,Vj), which is contained in a view Vj together with projection data g(CH3, Vj) that is found defective during scanning and which is produced on a channel CH2 or CH4 preceding or succeeding a channel on which the defective data is produced, for the defective data g(CH3,Vj). Consequently, the projection data g(CH2,Vj) or g(CH4,Vj) stemming from signals transmitted along paths that are close to a path, along which a signal providing the defective data is transmitted, in the direction of channels is substituted for the defective data g(CH3,Vj). Positional information on the substitute data is faithfully reflected on production of back projection data h(CH3,Vj).

According to the fifth aspect of the present invention, the data substitution means included in the CT apparatus in accordance with the second aspect substitutes projection data g(CHn−2,Vj'), which is contained in a view Vj' opposite to a view Vj containing projection data g(CH3,Vj) that is found defective during scanning and which is produced on a channel CHn−2 opposite to a channel on which the defective data is produced, for the defective data. Thus, the substitute data g(CHn−2,Vj') stemming from a signal that is transmitted along a transmission line Lj' substantially equivalent to a transmission line Lj along which an error signal is transmitted is sampled from the opposite view Vj'.

According to the sixth aspect of the present invention, the data interpolation means included in the CT apparatus in accordance with the third or fourth aspect thereof interpolates back projection data h(CH3,Vj) by calculating a weighted mean of projection data items g(CH4,Vk) and g(CH3,Vj'), which are produced by scanning sections of a subject, which precede or succeed a section Si in a body-axis direction, at substantially identical view angles Vk and Vj', as a predetermined function inversely proportional to or based on a distance c or b from a position represented by the interpolated data. Consequently, the value of the substitute data g(CH4, Vk) and the distance c to the position that are contained in the interpolated data are faithfully reflected. Eventually, a tomographic image can be reconstructed more accurately.

According to the seventh aspect of the present invention, the data interpolation means included in the CT apparatus in accordance with the fifth aspect thereof interpolates back projection data by calculating a weighted mean of projection data items, which are produced on opposite channels by scanning sections of a subject that precede or succeed a section concerned in a body-axis direction and which are contained in opposite views, inversely proportionally to a distance from a position represented by the interpolated data. Thus, projection data items contained in opposite views are used to properly interpolate back projection data.

According to the eighth aspect of the present invention, projection data found defective according to the second aspect thereof is projection data whose value is so small as to fall below a predetermined threshold among all projection data items constituting a certain view. Consequently, the poor sensitivity of a detector element can be effectively detected.

A program in accordance with the ninth aspect of the present invention is a computer-executable program for implementing the CT image reconstruction method in accordance with the first aspect of the present invention in a computer.

As mentioned above, according to the present invention, a CT image little affected by an artifact and expressing detected data more precisely than a conventional one can be produced.

Further objects and advantages of the present invention will be apparent from the following description of the preferred embodiments of the invention as illustrated in the accompanying drawings.

DETAILED DESCRIPTION OF THE INVENTION

Figure 1:
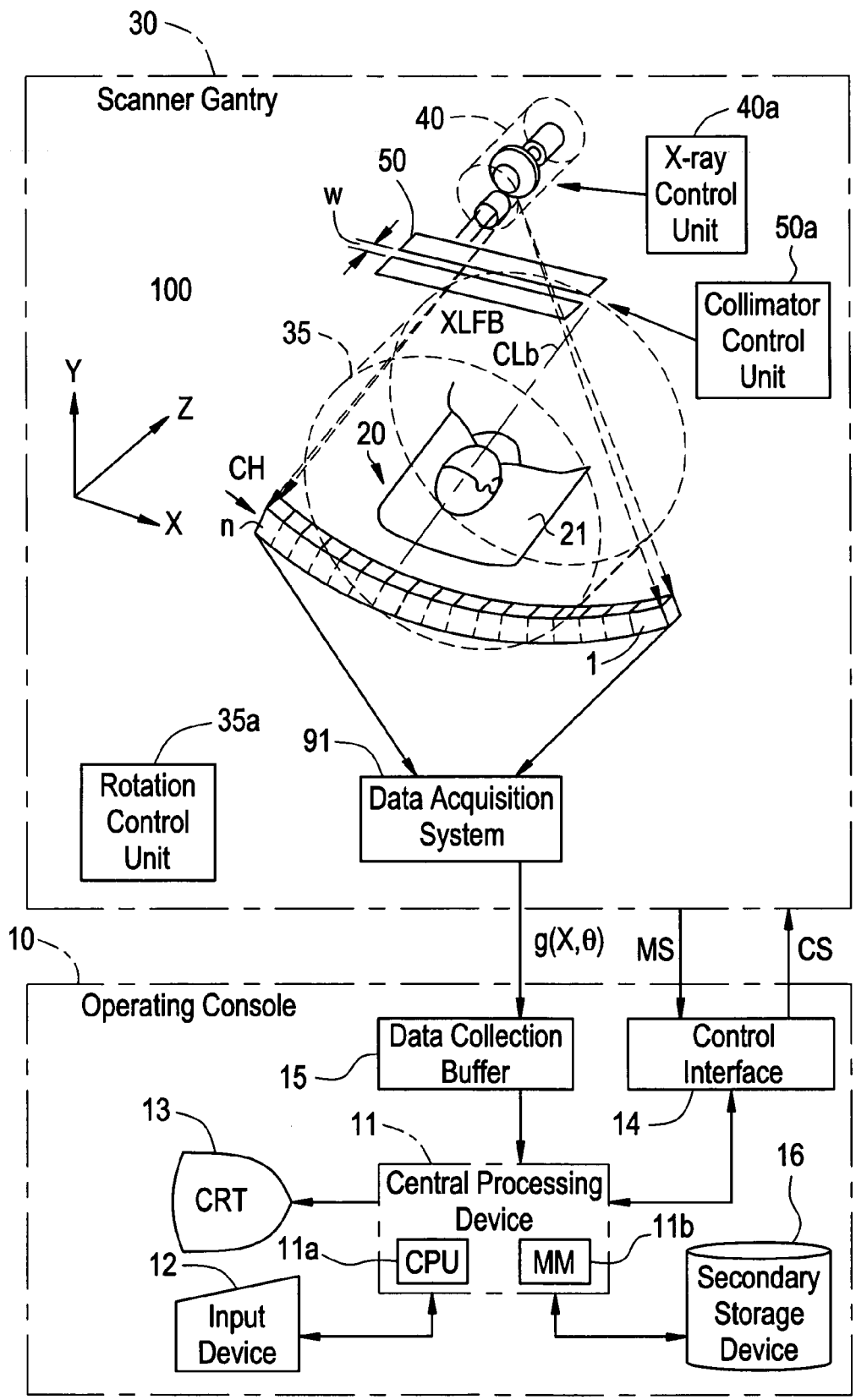
FIG. 1 shows the configuration of a major portion of an X-ray CT apparatus in accordance with an embodiment of the present invention.

A preferred embodiment of the present invention will be described below in conjunction with appended drawings. In all the drawings, the same reference numerals denote the same or equivalent components. FIG. 1 shows the configuration of a major portion of an X-ray CT apparatus in accordance with the embodiment. The X-ray CT apparatus comprises a scanner gantry 30 that scans a subject 100 with an X-ray fan-shaped beam XLFB and interprets data, a radiographic table 20 that carries the subject 100 in the directions of a body axis CLb, and an operator console 10 that remotely controls the gantry 30 and table 20 and which an operator or the like manipulates.

In relation to the scanner gantry 30, reference numeral 40 denotes a rotating anode X-ray tube, and reference numeral 40A denotes an X-ray control unit. Reference numeral 50 denotes a collimator that limits a slice width that is the width of X-rays in a body-axis direction, and reference numeral 50A denotes a collimator control unit. Reference numeral 90 denotes an X-ray detector having numerous (n=about 1000) X-ray detector elements set in array in a direction of channels CH. Reference numeral 91 denotes a data acquisition system (DAS) that produces or acquires projection data of a subject on the basis of a signal detected by the X-ray detector 90. Reference numeral 35 denotes a gantry that supports the X-ray imaging system so that the X-ray imaging system can rotate about the body axis of a subject. Reference numeral 35A denotes a rotation control unit for the gantry 35.

The radiographic table 20 has a tabletop (cradle) 21 on which the subject lies down and which carries the subject into or out of a bore of the scanner gantry 30. The cradle 21 is lifted or lowered and rectilinearly moved by a motor that is not shown and incorporated in the radiographic table 20.

In relation to the operator console 10, reference numeral 11 denotes a central processing device that is responsible for main control and processing (scanning control and reconstruction of a CT image) in the X-ray CT apparatus, reference numeral 11a denotes a central processing unit (CPU), and reference numeral 11b denotes a main memory (MM) realized with a RAM or a ROM to be used by the CPU 11a. Reference numeral 12 denotes an input device that includes a keyboard and a mouse and is used to enter a command or data. Reference numeral 13 denotes a display device (CRT) on which information on a scanning schedule or a CT image is displayed. Reference numeral 14 denotes a control interface via which the CPU 11a transfers various control signals CS and a monitor signal MS to or from the scanner gantry 30 or radiographic table 20. Reference numeral 15 denotes a data collection buffer in which projection data sent from the data acquisition system 91 is tentatively stored. Reference numeral 16 denotes a secondary storage device (hard disk drive or the like) in which various application programs that are needed to operate the X-ray CT apparatus and various data files for arithmetic operations or corrections are stored.

Owing to the foregoing components, the X-ray fan-shaped beam XLFB radiated from the X-ray tube 40 is irradiated to the subject 100 who is positioned in the bore of the scanner gantry 30. In this state, the X-ray fan beam XLFB radiated from the X-ray tube 40 is transmitted by the subject 100 and routed to the X-ray detector 90. The data acquisition system 91 produces projection data $g(X,\theta)$ from an output of the X-ray detector 90. The projection data is stored in the data collection buffer 15. Herein, X denotes a channel number in the detector, and $\theta$ denotes a view angle.

Furthermore, at each view angle $\theta$ at which the scanner gantry 35 stays after being slightly rotated, X-rays are projected. Thus, projection data items are acquired and stored during one turn of the scanner gantry. At the same time, the radiographic table 20 is intermittently or continuously moved in the direction of the body axis CLb according to the axial or helical scan technique. Thus, all projection data items representing a given scan field in a subject are acquired and then stored. The projection data items are preserved in the secondary storage device 16. The CPU 11a reconstructs a CT tomographic image of the subject on the basis of the projection data items produced after all the scans are completed or produced in parallel with scanning. The CT tomographic image is then displayed on the display device 13.

Figure 2:
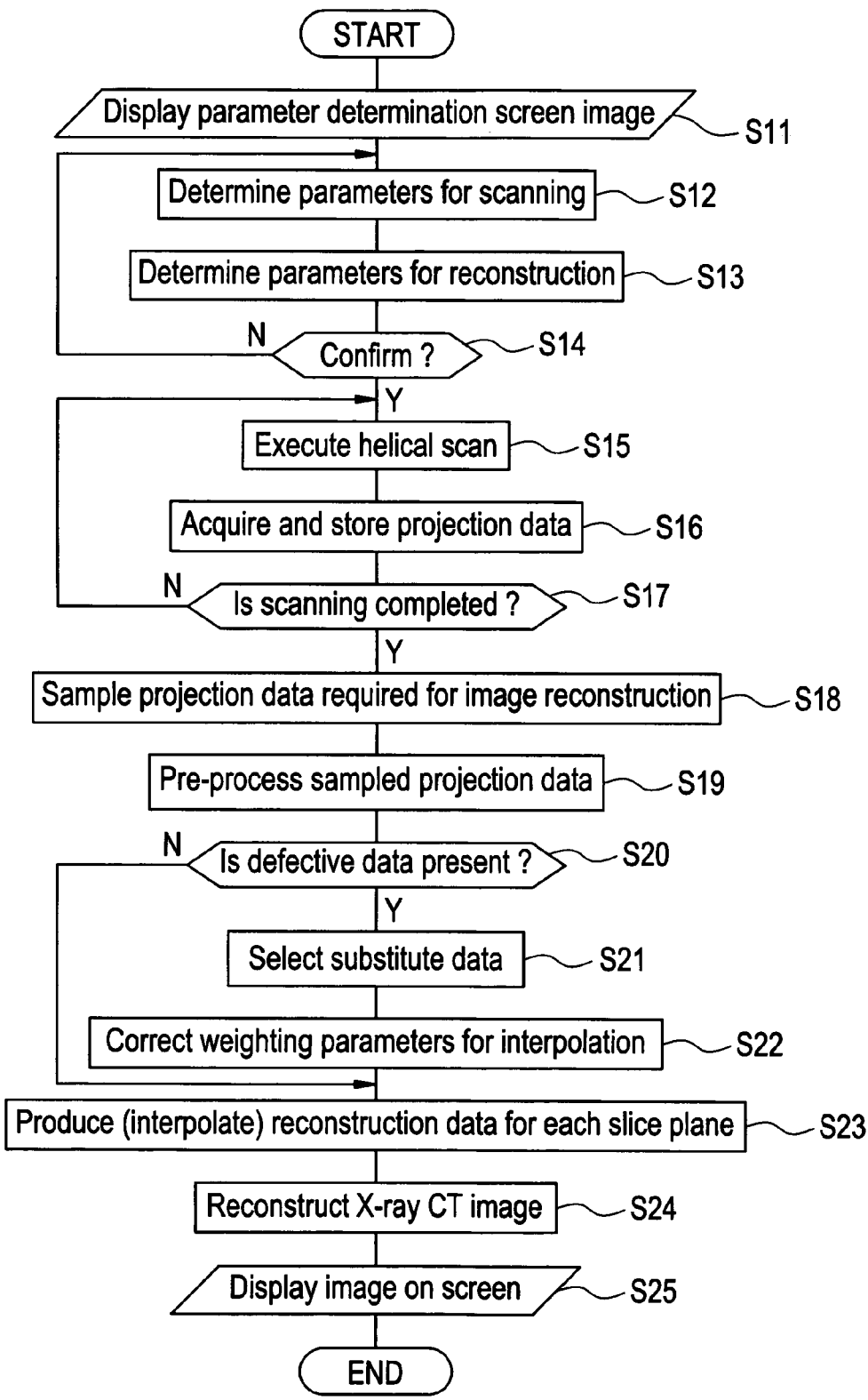
FIG. 2 is a flowchart describing X-ray CT performed in the embodiment.

Next, a flow of X-ray CT will be described below. FIG. 2 is a flowchart describing the X-ray CT in accordance with the present embodiment, thus presenting the application of the present invention to a case where defective data is accidentally produced. Preferably, a scout scan is performed on the subject 100 in advance, and the X-ray CT is then executed. At step S11, a parameter determination screen image for use in determining parameters required for imaging of the subject 100 is displayed on the display unit 13. At step S12, an operator or the like determines the parameters for scanning. At step S13, the operator determines the parameters for reconstructing a CT image. At step S14, the press of a Confirm button that is a parameter value confirmation button is waited. As long as the Confirm button is not pressed, control may be returned to step S12 at which the parameters for scanning or reconstruction can be modified.

If the Confirm button is pressed at step S14, the subject 100 is scanned (for example, helically scanned) according to the determined parameters for scanning at step S15. At step S16, projection data representing the subject 100 is acquired and stored. At step S17, whether all scans are completed for a given scan field is verified. If all scans are not completed, control is returned to step S15.

Figure 3:
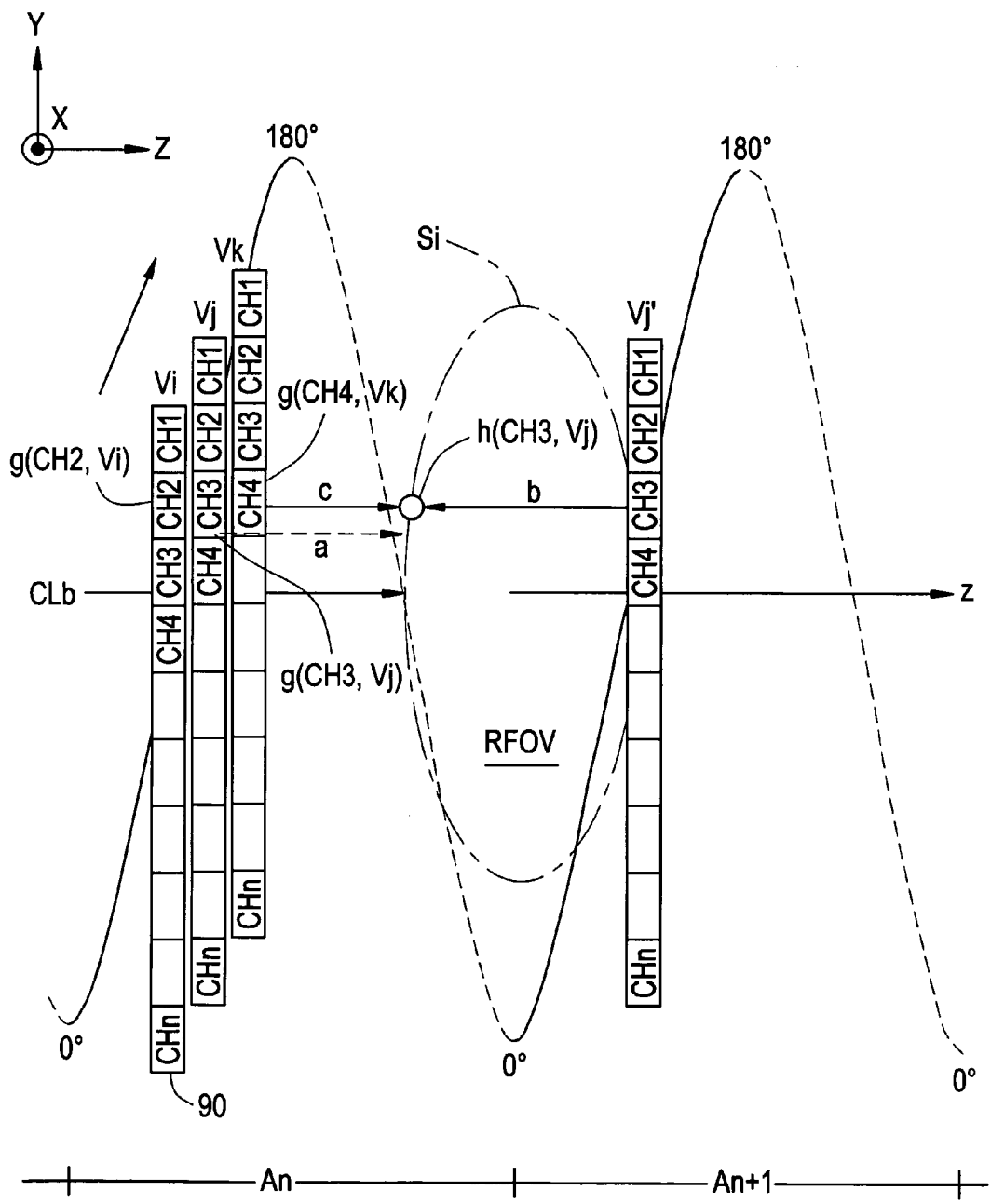
FIG. 3 imaginatively shows image reconstruction in accordance with the embodiment (part 1).

If all scans are completed, projection data items required for reconstruction of an image of each slice plane are sampled according to the determined parameters for reconstruction. Referring to FIG. 3, back projection data $h(X,\theta)$ required for reconstruction of an image of a certain slice plane Si is interpolated using projection data items produced during scans An and An+1. At step S19, predetermined preprocessing (correction of a variation in an X-ray output or correction of a difference in sensitivity between channels) is performed on the sampled projection data items.

At step S20, whether defective data is present is verified. For example, if a view contains certain channel data whose value is as small as to fall below a predetermined threshold, the data is regarded as defective data. The defective data is detected in all the projection data items sampled at step S118.

Figure 4:
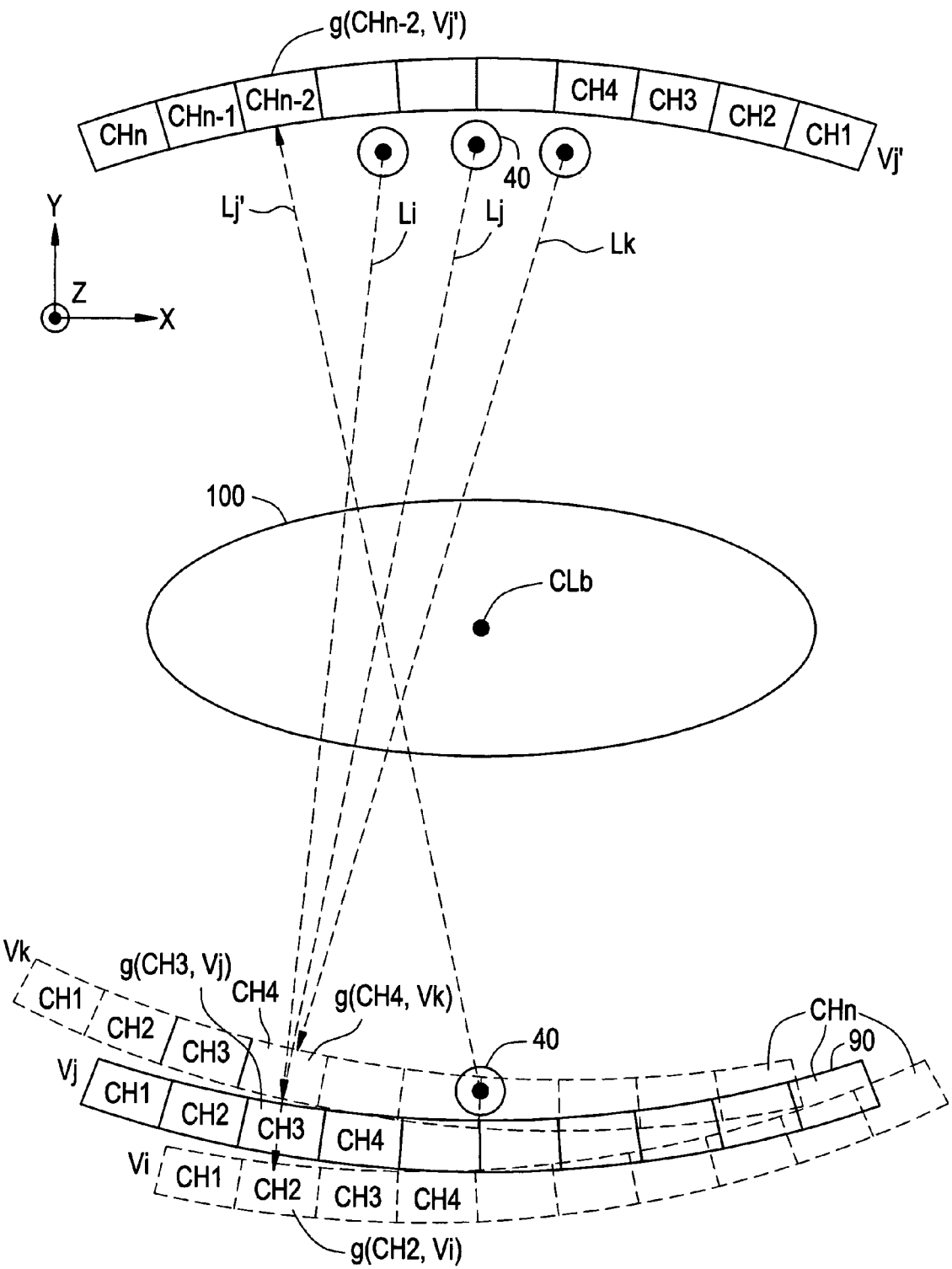
FIG. 4 imaginatively shows the image reconstruction in accordance with the embodiment (part 2).

At step S21, substitute data capable of being substituted for the detected defective data is selected. Referring to FIG. 4, assuming that projection data g(CH3,Vj) is defective, projection data g(CH2,Vi) or g(CH4,Vk) contained in a view Vi or Vk preceding or succeeding a view Vj which contains the defective data g(CH3,Vj), and produced on a channel CH2 or CH4 adjoining to the channel on which the defective data is produced is preferably substituted for the defective data g(CH3,Vj). Thus, other projection data g(CH2,Vi) or g(CH4,Vk) stemming from a signal transmitted along a path close to a path, along which a signal providing the defective data is transmitted, in a body-axis direction is substituted for the defective data g(CH3,Vj). Moreover, positional information on the substitute data is faithfully reflected on production of back projection data h(CH3,Vj).

Otherwise, projection data g(CH2,Vj) or g(CH4,Vj) contained in a view Vj together with the defective data g(CH3,Vj) and produced on a channel CH2 or CH4 preceding or succeeding the channel on which the defective data is produced is substituted for the defective data. Thus, the projection data g(CH2,Vj) or g(CH4,Vj) stemming from a signal transmitted along a path close to a path, along which a signal providing the defective data is transmitted, in the direction of channels is substituted for the defective data. Moreover, positional information on the substitute data is faithfully reflected on production of back projection data h(CH3,Vj).

Otherwise, projection data g(CHn−2,Vj') contained in a view Vj' opposite to a view Vj containing the defective data g(CH3,Vj), and produced on a channel CHn−2 opposite to a channel on which the defective data is produced is substituted for the defective data. Thus, the substitute data g(CHn−2,Vj') stemming from a signal transmitted along a line Lj' substantially equivalent to a line Lj along which an error signal is transmitted is sampled from the opposite view.

At step S22, the weighting parameter for interpolation is corrected. A case will be described concretely. Referring to FIG. 3, back projection data h(CH3,Vj) is produced by calculating a weighted mean of projection data items g(CH3,Vj) and g(CH3,Vj'), which are produced by scanning slice planes, which precede or succeed a slice plane Si in the direction of a body axis, at the same view angles Vj and Vj', inversely proportionally to a distance a or b from the slice plane Si according to the following expression:

$$h(CH3,Vj)=\{b \cdot g(CH3,Vj)+a \cdot g(CH3,Vj')\}/(a+b)$$

Assuming that projection data g(CH3,Vj) is defective, projection data g(CH4,Vk) contained in an adjoining view is substituted for the defective data. In this case, the weighting parameter for interpolation is changed from a to c. Back projection data h(CH3,Vj) is calculated as follows:

$$h(CH3,Vj)=\{b \cdot g(CH4,Vk)+c \cdot g(CH3,Vj')\}/(c+b)$$

Consequently, the back projection data faithfully reflects the value of the substitute data g(CH4,Vk) and the distance c to the slice plane Si. A more accurate tomographic image can be reconstructed. The same applies to a case where projection data g(CH4,Vi) is substituted for the defective data g(CH3,Vj).

On the other hand, when adjoining projection data g(CH2, Vj) or g(CH4,Vj) contained in the same view as the view containing the defective data g(CH3,Vj) is substituted for the defective data, the distance to a position represented by interpolated data is corrected according to $\sqrt{(a^2+\Delta CH^2)}$. Herein, $\Delta CH$ denotes an inter-channel distance.

As shown in FIG. 4, when opposite projection data g(CHn−2,Vj') contained in an opposite view is substituted for the defective data g(CH3,Vj), since transmission paths Lj and Lj' are substantially equivalent to each other, the distance to a position represented by interpolated data is regarded as the distance a.

The calculation method adapted to a case has been described concretely. Any of other various known methods (functions) can be adopted as the method of calculating interpolated data. Whichever of the methods is adopted, if weighting factors to be used to reconstruct an image are prepared in the form of a table, the weighting factors are re-calculated based on positional information on defective data. If the weighting factors are not prepared, the weighting factors are calculated (produced) by reflecting the positional information on defective data.

Referring back to FIG. 2, if absence of defective data is verified at step S20, steps S21 and S22 are skipped. At step S23, image reconstruction data $h(X,\theta)$ representing each slice plane is interpolated according to a known method. At step S24, an X-ray CT image is reconstructed. At step S25, produced CT images are displayed on the screen.

According to the present embodiment, defective data is accidentally produced. The present invention is not limited to this case. The present invention can be applied to a case where defective data is always produced on a certain channel because of a defective detector element (cell). In this case, preferably, before scanning is initiated, information on the defective cell is acquired, information on data produced by a cell adjoining the defective cell is also acquired, and the pieces of information are listed in the form of a table. If weighting factors to be used to reconstruct an image are prepared in the form of a table, the positional information on the adjoining data is used to re-calculate the weighting factors to be used to reconstruct an image. If the weighting factors are not prepared, the weighting factors are calculated by reflecting the information on the defective cell. Scanning is then initiated. Reconstruction data can be readily produced using the calculated weighting factors.

The embodiment has been described concretely on the assumption that the present invention is applied to image reconstruction to be performed using the single-array X-ray detector 90. The present invention is not limited to the mode. Apparently, the present invention can be applied to image reconstruction to be performed using a multi-channel detector having two or more detector arrays.

The embodiment has been described on the assumption that the present invention is applied to the helical scan technique. The present invention is not limited to the technique. Even when the axial scan technique is adopted, back projection data may be interpolated for each slice plane. The present invention can be applied to this case.

The embodiment has been described on the assumption that back projection data is interpolated relative to projection data produced at each of view angles ending with 360°. The present invention can be applied to a so-called half reconstruction method.

The embodiment has been described on the assumption that the present invention is adapted to an X-ray CT apparatus. The present invention is not limited to this mode. The present invention may be constructed as software that implements the CT image reconstruction method in a computer. The software may be recorded in an information recording medium such as a CD or provided through online communication over a wired or wireless communication line.

Many widely different embodiments of the invention may be configured without departing from the spirit and the scope of the present invention. It should be understood that the present invention is not limited to the specific embodiments described in the specification, except as defined in the appended claims.

The invention claimed is:

1. A Computer Tomography (CT) image reconstruction method for reconstructing a CT image based on scan projection data obtained by scanning a subject, said CT image reconstruction method comprising:
   replacing a value of defective projection data of the scan projection data with substitute projection data of the scan projection data, the substitute projection data having a transmission path adjacent to a transmission path of the defective projection data and positional information related to a scan that is different from positional information of the defective projection data; and
   calculating a back projection based on the scan projection data using a parameter based on the positional information related to the scan, and including calculating the back projection based on the replaced defective projection data value using the parameter based on the positional information of the substitute projection data.

2. A CT image reconstruction method according to claim 1, further comprising obtaining back projection data using a weighted calculation of the scan projection data having a position that one of precedes a CT image plane to be reconstructed and succeeds the CT image plane to be reconstructed based on a distance from the position of the scan projection data to the CT image plane obtained by the positional information thereof.

3. A CT image reconstruction method according to claim 1, further comprising determining defective projection data having a value less than a predetermined threshold of scan projection data values contained in a certain view.

4. A CT image reconstruction method according to claim 1, wherein replacing defective projection data of the scan projection data with substitute projection data of the scan projection data comprises replacing the defective projection data with substitute projection data contained in a view one of preceding a view containing the defective projection data and succeeding a view containing the defective projection data and having a transmission path adjacent to the transmission path of the defective projection data.

5. A CT image reconstruction method according to claim 1, wherein replacing defective projection data of the scan projection data with substitute projection data of the scan projection data comprises replacing the defective projection data with substitute projection data contained in a view opposite to a view containing the defective projection data and that is produced on a channel opposite to a channel on which the defective projection data is produced.

6. A Computer Tomography (CT) apparatus comprising:
   a scanning device configured to scan a subject and to obtain scan projection data; and
   a reconstructing device configured to reconstruct a CT image based on the scan projection data, said reconstructing device comprising:

a data replacement device configured to replace a value of defective projection data of the scan projection data with substitute projection data of the scan projection data, the substitute projection data having a transmission path adjacent to a transmission path of the defective projection data and positional information related to a scan that is different from positional information of the defective projection data; and a data calculating device configured to calculate back projection data based on the scan projection data using a parameter based on the positional information related to the scan, the back projection data calculation further including a calculation based on the replaced defective projection data value using the parameter based on the positional information of the substitute projection data.

7. The CT apparatus according to claim 6, wherein said data replacement device is further configured to replace the defective projection data with substitute projection data that is contained in a view one of preceding a view containing the defective projection data and succeeding a view containing the defective projection data and having a transmission path adjacent to the transmission path of the defective projection data.

8. The CT apparatus according to claim 6, wherein said data replacement device is further configured to replace the defective projection data with substitute projection data that is contained in a view opposite to a view containing the defective projection data and that is produced on a channel opposite to a channel on which the defective projection data is produced.

9. The CT apparatus according to claim 6, wherein said data calculating device comprises a data interpolation device configured to obtain back projection data using a weighted calculation of the scan projection data having a position that one of precedes a CT image plane to be reconstructed and succeeds the CT image plane to be reconstructed based on a distance from the position of the scan projection data to the CT image plane obtained by the positional information thereof.

10. The CT apparatus according to claim 9, wherein said scanning device is configured to scan the subject using a helical scan.

11. The CT apparatus according to claim 6, wherein the defective projection data has a value less than a predetermined threshold of scan projection data values contained in a certain view.

12. The CT apparatus according to claim 6, wherein said data replacement device is further configured to replace the defective projection data with substitute projection data contained in a view containing the defective projection data and having a transmission path adjacent to the transmission path of the defective projection data.

13. A computer-readable medium encoded with a computer program for reconstructing a Computer Tomography (CT) image based on scan projection data obtained by scanning a subject, wherein the computer program comprises at least one code segment that:

replaces a value of defective projection data of the scan projection data with substitute projection data of the scan projection data, the substitute projection data having a transmission path adjacent to a transmission path of the defective projection data and positional information related to a scan that is different from positional information of the defective projection data;

calculates a back projection based on the scan projection data using a parameter based on the positional information related to the scan, and including calculating the back projection based on the replaced defective projection data value using the parameter based on the positional information of the substitute projection data; and reconstructs a CT image based on the calculated back projection for display to an operator of a CT apparatus.

14. A computer-readable medium encoded with a computer program according to claim 13, wherein the computer program further comprises at least one code segment that determines defective projection data having a value less than a predetermined threshold of scan projection data values contained in a certain view.

15. A computer-readable medium encoded with a computer program according to claim 13, wherein the computer program further comprises at least one code segment that replaces the defective projection data with substitute projection data that is contained in a view one of preceding a view containing the defective projection data and succeeding a view containing the defective projection data and having a transmission path that is adjacent to the transmission path of the defective projection data.

16. A computer-readable medium encoded with a computer program according to claim 13, wherein the computer program further comprises at least one code segment that replaces the defective projection data with substitute projection data that is contained in a view containing the defective projection data and having a transmission path that is adjacent to the transmission path of the defective projection data.

17. A computer-readable medium encoded with a computer program according to claim 13, wherein the computer program further comprises at least one code segment that replaces the defective projection data with substitute projection data that is contained in a view opposite to a view containing the defective projection data and that is produced on a channel opposite to a channel on which the defective projection data is produced.

18. A computer-readable medium encoded with a computer program according to claim 13, wherein the computer program further comprises at least one code segment that determines back projection data using a weighted calculation of the scan projection data having a position that one of precedes a CT image plane to be reconstructed and succeeds the CT image plane to be reconstructed based on a distance from the position of the scan projection data to the CT image plane obtained by positional information thereof.

* * * * *

UNITED STATES PATENT AND TRADEMARK OFFICE
CERTIFICATE OF CORRECTION

PATENT NO. : 7,580,501 B2  Page 1 of 1
APPLICATION NO. : 11/214503
DATED : August 25, 2009
INVENTOR(S) : Hagiwara et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 244 days.

Signed and Sealed this

Fourteenth Day of September, 2010

David J. Kappos
*Director of the United States Patent and Trademark Office*